(12) United States Patent
Dews

(10) Patent No.: US 6,197,063 B1
(45) Date of Patent: Mar. 6, 2001

(54) MODULAR HUMERAL PROSTHESIS AND METHOD

(75) Inventor: Paul M. Dews, Leeds (GB)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 09/054,709

(22) Filed: Apr. 3, 1998

(30) Foreign Application Priority Data

Apr. 11, 1997 (GB) .................................................. 9707371

(51) Int. Cl.⁷ ...................................................... A61F 2/40
(52) U.S. Cl. ............................................................ 623/19.14
(58) Field of Search ................................. 623/16, 18, 19, 623/22, 23, 19.11, 19.14, 19.13, 22.42, 22.44, 22.45

(56) References Cited

U.S. PATENT DOCUMENTS

| | | |
|---|---|---|
| 3,694,820 | 10/1972 | Scales et al. . |
| 3,803,641 | 4/1974 | Golyakhovsky . |
| 3,916,451 | 11/1975 | Buechel et al. . |
| 3,978,528 | 9/1976 | Crep . |
| 4,003,095 | 1/1977 | Gristina . |
| 4,040,131 | 8/1977 | Gristina . |
| 4,045,825 | 9/1977 | Stroot . |
| 4,106,130 | 8/1978 | Scales . |

(List continued on next page.)

FOREIGN PATENT DOCUMENTS

| | | |
|---|---|---|
| 29 32 744 | 8/1978 | (DE) . |
| 44 01 952 C1 | 1/1994 | (DE) . |

(List continued on next page.)

OTHER PUBLICATIONS

"Glenohumeral Arthroplasty" p. 148–150.
"Surgical Protocol Modular Shoulder" brochure, 3M Health Care Ltd. 1994.
"Product Specification" brochure, 3M Health Care Ltd. 1994.

(List continued on next page.)

Primary Examiner—Gene Mancene
Assistant Examiner—Eduardo C. Robert
(74) Attorney, Agent, or Firm—James L. Ewing, IV; Kristin D. Mallatt; Kilpatrick Stockton LLP

(57) ABSTRACT

A modular humeral prosthesis for replacement of the humeral head of a humerus. The prosthesis generally comprises a stem to be fitted to a resected humerus; a head sized and configured to approximate the humeral head; and an intermediate connecting member for connecting the stem to the head. A first engagement/mounting portion is provided on the intermediate connecting member for mounting the intermediate connecting member on the stem, and a second engagement/mounting portion is provided on the intermediate connecting member for mounting the head on the intermediate connecting member. The first engagement/mounting portion has an axis about which the intermediate connecting member can be rotated through 360° relative to the stem and thereafter secured at a selected relative orientation. The second engagement/mounting portion has an axis about which the head can be rotated through 360° relative to the intermediate connecting member and thereafter secured at a selected relative rotation. The axis of rotation of the first and second engagement/mounting portions are not coincident, whereby the first and second engagement/mounting portions allow the head to be given a desired offset relative to the stem. Also disclosed is a modular humeral prosthesis kit comprising a variety of different intermediate connecting members that may be selected to fit the prosthesis to the patient, and a method of replacing a humeral head in a patient.

38 Claims, 5 Drawing Sheets

U.S. PATENT DOCUMENTS

| | | | |
|---|---|---|---|
| 4,135,517 | * | 1/1979 | Reale ............................................ 623/23 |
| 4,179,758 | | 12/1979 | Gristina . |
| 4,206,517 | | 6/1980 | Pappas et al. . |
| 4,219,893 | | 9/1980 | Noiles . |
| 4,279,041 | | 7/1981 | Buchholz . |
| 4,301,553 | | 11/1981 | Noiles . |
| 4,352,212 | | 10/1982 | Greene et al. . |
| 4,538,305 | | 9/1985 | Engelbrecht et al. . |
| 4,549,319 | | 10/1985 | Meyer . |
| 4,608,053 | | 8/1986 | Keller . |
| 4,634,444 | | 1/1987 | Noiles . |
| 4,650,489 | | 3/1987 | Thompson . |
| 4,676,797 | * | 6/1987 | Anapliotis et al. ............... 623/23 |
| 4,693,723 | | 9/1987 | Gebard . |
| 4,822,370 | | 4/1989 | Schelhas . |
| 4,865,605 | | 9/1989 | Dines et al. . |
| 4,892,546 | | 1/1990 | Kotz et al. . |
| 4,908,032 | | 3/1990 | Keller . |
| 4,911,719 | | 3/1990 | Merle . |
| 4,919,669 | | 4/1990 | Lannelongue . |
| 4,919,670 | | 4/1990 | Dale et al. . |
| 4,921,500 | * | 5/1990 | Averill et al. ................. 623/22.45 |
| 4,938,773 | | 7/1990 | Strand . |
| 4,957,510 | | 9/1990 | Cremascoli . |
| 4,963,155 | | 10/1990 | Lazzeri et al. . |
| 4,986,833 | | 1/1991 | Worland . |
| 5,002,578 | | 3/1991 | Luman . |
| 5,002,581 | | 3/1991 | Paxson et al. . |
| 5,015,257 | * | 5/1991 | Crowninshield et al. ........ 623/22.45 |
| 5,201,882 | | 4/1993 | Paxson . |
| 5,282,865 | | 2/1994 | Dong . |
| 5,314,479 | * | 5/1994 | Rockwoos, Jr. et al. ............... 623/19 |
| 5,358,526 | | 10/1994 | Tornier . |
| 5,462,563 | | 10/1995 | Shearer et al. . |
| 5,489,309 | | 2/1996 | Lackey et al. . |
| 5,507,814 | * | 4/1996 | Gilbert et al. .......................... 623/16 |
| 5,507,817 | | 4/1996 | Craig et al. . |
| 5,507,818 | | 4/1996 | McLaughlin . |
| 5,549,682 | | 8/1996 | Roy . |
| 5,549,703 | * | 8/1996 | Daigle et al. ........................ 623/23 |
| 5,580,352 | * | 12/1996 | Sekel ....................................... 623/23 |
| 5,658,340 | | 8/1997 | Muller et al. . |
| 5,702,457 | | 12/1997 | Walch et al. . |
| 5,702,486 | | 12/1997 | Craig et al. . |
| 5,728,161 | | 3/1998 | Camino et al. . |
| 5,902,340 | * | 5/1999 | White et al. ........................ 623/19 |
| 5,906,644 | * | 5/1999 | Powell .................................. 623/23 |
| 6,129,764 | | 10/2000 | Servidio . |

FOREIGN PATENT DOCUMENTS

| | | | |
|---|---|---|---|
| 4320086 | * | 12/1994 | (DE) ....................................... 623/23 |
| 195 09 037 C1 | | 3/1995 | (DE) . |
| 0 041 591 A1 | | 5/1980 | (EP) . |
| 0099167 | * | 1/1984 | (EP) ....................................... 623/23 |
| 0 127 503 A1 | | 12/1984 | (EP) . |
| 0 201 407 A1 | | 11/1986 | (EP) . |
| 0 201 407 B1 | | 11/1986 | (EP) . |
| 0 216 489 A1 | | 4/1987 | (EP) . |
| 0 278 807 A3 | | 8/1988 | (EP) . |
| 0 299 889 A3 | | 1/1989 | (EP) . |
| 0 299 889 B1 | | 1/1989 | (EP) . |
| 0 485 311 A1 | | 5/1992 | (EP) . |
| 0 639 359 A1 | | 8/1993 | (EP) . |
| 0 599 429 A2 | | 6/1994 | (EP) . |
| 0 664 108 A2 | | 7/1995 | (EP) . |
| 0 679 375 A1 | | 11/1995 | (EP) . |
| 0 712 617 A1 | | 5/1996 | (EP) . |
| 2 617 706 | | 1/1989 | (FR) . |
| 2 647 670 | | 12/1990 | (FR) . |
| 2 652 498 | | 4/1991 | (FR) . |
| 2 664 809 | | 1/1992 | (FR) . |
| 2697996 | * | 5/1994 | (FR) ....................................... 623/23 |
| 2 721 200 | | 12/1995 | (FR) . |
| 1 292 561 | | 10/1972 | (GB) . |
| 1 438 950 | | 6/1976 | (GB) . |
| 1 548 750 | | 7/1979 | (GB) . |
| 2 223 172 | | 4/1990 | (GB) . |
| WO 96/17553 | | 6/1994 | (WO) . |
| WO 94/15551 | | 7/1994 | (WO) . |
| WO 95/22302 | | 8/1995 | (WO) . |
| WO 96/38104 | | 12/1996 | (WO) . |
| WO 96/41597 | | 12/1996 | (WO) . |

OTHER PUBLICATIONS

"3M Modular Shoulder Ideas in Motion" brochure, 3M Health Care Ltd. 1994.

"Neer II Total Shoulder System" brochure, 3M Health Care Ltd. 1989.

Biomet, Inc.—Shoulder Systems, http://www.biomet/com/product/shoulder.html ((c) 1997), plus pages on Bio–Modular ™, Bi–Angular™, Bi–Angular/Bi–Polar™, Integrated Shoulder System™, and Proximal Humeral Replacement™.

DePuy, Product Information: Global™ Total Shoulder System, http://www.depuy.com/products/global.htm (last updated Mar. 13, 1998).

Homedica: MRS, http://www.howmedica.com./mrs/shoulder.htm, http://www.howmedica.com/mrs/shoulder1.htm, http://www.howmedica.com/mrs/shoulder2.htm, http://www.howmedica.com/mrs/shoulder3.htm (printed May 29, 1998).

Daniel E. Williamson, M.S., Design Considerations in Total Shoulder Arthroplasty Relating to Long–Term Glenohumeral Stability((c) 1994 Biomet, Inc.).

* cited by examiner

MODULAR HUMERAL PROSTHESIS AND METHOD

BACKGROUND OF THE INVENTION

During the procedure of a shoulder replacement operation, at least a portion of the proximal section of the humeral shaft will be replaced by a metal prosthesis. This prosthesis will generally consist of two parts: a stem that is mounted into the medullary canal of the humerus, and a head component connected in some manner to the stem. The head component replaces the bearing surfaces of the humerus and articulates with the surface of the scapula to allow the movement of the shoulder.

Modular humeral prostheses are known. The stem and head component may be supplied in "modular" form, that is, as separate connectable components. Different stem sizes and head sizes in a modular implant design provide the surgeon with some degree of inter-operative flexibility, which facilitates reconstruction of the original anatomy of the patient.

With a range of stem sizes and a range of head sizes available, the surgeon can choose a particular combination to suit the anatomy of each individual patient without having to have a large inventory of "integral" or "unitary" humeral prosthesis. As used herein, "integral" and "unitary" mean formed in one continuous piece in contrast to the separate connectable components of a modular prosthesis. For example, one patient might require a relatively small head and a relatively long stem. With a unitary prosthesis a wide range of stem lengths would be required for each head size whereas with a modular arrangement a particular head can be used with a range of stem sizes and visa versa.

Additional variations arise also as a result of individual patients requiring differing angles of inclination of the head relative to the stem and of differing offsets between the axis of the head and the axis of the stem. Thus, in one patient the offset may be posterior and in another anterior.

Various shoulder prostheses are disclosed in European Patent Publication No. EP-A 0 679 375; EP-A 0 712 617; French Patent No. FR-A 2 664 809; U.S. Pat. Nos. 3,694,820; 3,803,641; 4,045,825; 4,106,130; 4,179,758; 4,865,605; 4,919,670; 5,358,526; 5,549,682; 5,462,563 and 5,702,457; and PCT International Patent Publication No. WO 96/17553.

SUMMARY OF THE INVENTION

This invention provides a modular prosthesis in which a humeral head, chosen to suit a patient, is attached to a stem chosen to suit the resected humerus of the patient by means of an intermediate connecting member. The prosthesis can accommodate a wide range of variation, in a relatively cheap manner, by providing the variations required in the intermediate connecting member rather than in the very much more expensive head.

The modular humeral prosthesis generally comprises a stem to be fitted to a resected humerus, a head sized and configured to approximate the humeral head, and an intermediate connecting member for connecting the stem to the head. The intermediate connecting member includes first engagement means for mounting the intermediate connecting member on the stem. The first engagement means has an axis about which the intermediate connecting member can be rotated through 360° relative to the stem and thereafter secured at a selected relative orientation. The intermediate connecting member further includes second engagement means for mounting the head on the intermediate connecting member. The second engagement means has an axis about which the head can be rotated through 360° relative to the intermediate connecting member and thereafter secured at a selected relative rotation. The axis of rotation of the first and second engagement means is not coincident, whereby the first and second engagement means allow the head to be given a desired offset relative to the stem.

Preferably, the axis of rotation of the first and second engagement means are not parallel, whereby the engagement means allow a desired inclination of the head relative to the stem.

Also, preferably, the first and second engagement means of the intermediate connecting member are positioned relative to one another to provide a desired separation between the head and the stem.

The first and second engagement means of the intermediate connecting member are preferably positioned relative to one another to provide a desired separation between the head and the stem. Most preferably, the separation or "neck length" between the head and the stem is no greater than 5 mm.

Also, preferably, the first and second engagement means each comprise a male portion, and the head and stem are provided with corresponding mating female portions. The male and female portions preferably each have a substantially circular cross-sections, and a substantially self-locking tapered configuration (i.e., a Morse taper).

Most preferably, a bore is provided through the first and second engagement means and extends through the intermediate connecting member, and the prosthesis further comprising a fastener inserted through the bore to engage the stem to further secure the intermediate connecting member to the stem.

In a second aspect of the invention modular humeral prosthesis kit is provided for replacement of the humeral head of a humerus, The kit generally comprises a stem to be fitted to a resected humerus, a head sized and configured to approximate the humeral head, and a plurality of intermediate connecting members of which one may be selected to connect the stem to the head. Each intermediate connecting member includes first engagement means for mounting the intermediate connecting member on the stem, and second engagement means for mounting the head on the intermediate connecting member. The plurality of the intermediate connecting members of the kit include:

A. At least one intermediate connecting member in which the first and second engagement means have generally parallel and coincident central axii;

B. At least one intermediate connecting member in which the first and second engagement means have generally parallel but not coincident central axii;

C. At least one intermediate connecting member in which the first and second engagement means have an angle of inclination between one another that is different than the angle of inclination between the first and second engagement means of another intermediate connecting member of the kit; and D. At least one intermediate connecting member in which the first and second engagement means are separated by a different neck length than the neck length separating the first and second engagement means of another intermediate connecting member of the kit.

The specifications for the plurality of intermediate connecting members set out at A–D above may be met by combining features in some of the intermediate connecting member of the kit. For example, two intermediate connecting members may have different neck lengths, angles of inclination and offsets or zero offset.

Preferably, the first engagement means of each intermediate connecting member has an axis about which the intermediate connecting member can be rotated through 360° relative to the stem and thereafter secured at a selected relative orientation, and the second engagement means of each intermediate connecting member has an axis about which the head can be rotated through 360° relative to the intermediate connecting member and thereafter secured at a selected relative rotation.

Also, preferably, the first and second engagement means of each intermediate connecting member comprise male portions, and the head and stem are provided with corresponding mating female portions. Most preferably, the male and female portions each have a substantially circular cross-section, and a substantially self-locking tapered configuration (i.e., a Morse taper).

Most preferably, each intermediate connecting member is provided with a bore through the first and second engagement means, and the kit further comprises a fastener inserted through the bore to engage the stem to further secure the intermediate connecting member to the stem.

A third aspect of the invention is a method of replacing a humeral head in a patient. The method generally comprises:

(a) Resecting the proximal end of the humerus to remove the head and expose the medullary canal of the humerus;

(b) Inserting the stem of a prosthesis into the medullary canal of the resected humerus, the prosthesis being modular and comprising:

A stem;

A humeral head; and

One of a plurality of intermediate connecting members for connecting the stem to the head; each intermediate connecting member including:

First engagement means between the stem and the intermediate connecting member, the first engagement having an axis about which the intermediate connecting member can be rotated relative to the stem and thereafter secured at a selected relative orientation; and Second engagement means between the head and the intermediate connecting member;

The plurality of intermediate connecting members including connecting members having different inclination angles between the first and second engagement means and different amounts of offset or no offset between the first and second engagement means;

(c) Selecting a particular intermediate connecting member to provide a desired inclination of the head relative to the axis of a humerus and/or a desired offset of the head; and (d) Setting the intermediate connecting member at an orientation relative to the stem to give the desired inclination of the head relative to the axis of a humerus and/or a desired offset of the head.

Preferably, the plurality of intermediate connecting members includes intermediate connecting members having different neck lengths separating the first and second engagement means, and the method further comprising selecting an intermediate connecting member to provide a desired separation between the head and the stem.

Most preferably, the plurality of intermediate connecting members each have a bore extending through the intermediate connecting member between the first and second engagement means, and the method further comprises inserting a fastener into the bore through the second and first engagement means into engagement with the stem to further secure the intermediate member to the stem.

As can be seen, the surgeon will still need his traditional range of head sizes and stem sizes and lengths. However, the surgeon does not need additional heads or stems to provide a particular orientation of the head or a particular offset for the head. Thus, whilst a range of intermediate connecting members are required to be available to choose particular offsets and orientations, those intermediate connecting members are relatively cheap compared with the normally very high cost of the highly sophisticated head component.

Also, it is an advantage of the invention that the surgeon can choose quite independently of one another the three component parts. Thus, the surgeon does not have to be concerned with questions of offset and orientation when selecting the right head size. The same is true as regards the stem: the surgeon can choose the correct stem to fit the medullary canal in the humerus and so give a long lasting and secure joint between the stem and the bone. Having selected these components, the surgeon can, quite independently, decide on the particular offset and/or orientation of the head relative to the stem and select an intermediate connecting member accordingly. The surgeon is, therefore, able to match the modular prosthesis used to the original anatomy of a particular patient. Because a shoulder joint is enclosed and surrounded by soft tissue, it is desirable that the spacing between the end of the stem and the head be kept to a minimum, e.g. no greater than 5 mm.

The typical surgical procedure for the implantation of a humeral prosthesis includes the determination of the longitudinal axis of the humerus, drilling a hole in the proximal margin between the head and the tuberosity in line with this, then inserting a starter reamer or broach, and developing a bore hole along the longitudinal axis of the humerus. Next, this bore hole can be enlarged by using progressively larger reamers or broaches, until the surgeon determines that the reamer or broach being used is the largest possible fit into the available cavity without the excessive removal of cortical bone. Then, the head is accurately removed from the proximal portion of the humerus, and a flat angled face is prepared on the proximal portion of the humerus, usually along the line of the anatomical neck, by means of a resection guide.

The cavity thus prepared, the trial stem can be introduced. At this stage, the surgeon is able to determine the amount of anteversion that is appropriate for the patient. Once in place, the head measurement instrument can be attached, and the trial head attached to this. This head measurement instrument allows the accurate placement of the head in a number of different positions so that the surgeon to assess which position best suits the exact anatomy of the patient. Once determined, the surgeon can read off the specific orientation of the head from a number of scales on the instrument; this determines which intermediate connecting member is to be used with the definitive implant.

It is not possible to provide an infinite number of intermediate connecting members so as to cover every possibility of adjustment. In practical terms, therefore, one provides a range of intermediate connecting members in incremental sizes to provide a range of discrete adjustments in just the same way that a discrete number of heads and stems are provided. However, because the engagement means allows the relative rotation of the components, one can with a single intermediate connecting member choose an amount of offset and that amount can be positioned on a locus throughout 360°. The same, of course, is true as regards the inclination of the axis of the head relative to the stem.

In a preferred embodiment of the invention, the intermediate connecting member is available in a discrete number of sizes, each size providing an incremental increase in the separation between the two engagement means. Thus, the surgeon is provided with a variety of parts from which to choose in order to best approximate the patient's original anatomy by selecting a part that will provide the closest approximation of the original separation between the humeral head and the humeral stem.

It is preferred that each engagement means comprise a male projection on one part that fits within a complimentary female recess in the other. Preferably, at least the first engagement means, and in some embodiments of the invention the second engagement means as well, allows relative rotation of the respective parts. Therefore, they should be of circular cross-section.

It is further preferred that the second engagement means locate at the center of the base of the humeral head. Thus, in this preferred embodiment, the relative rotational placement of the head component has no effect in altering the angle of inclination of the head or the axial offset of the head in relation to the stem or even the separation between the head and the stem. Indeed it is not essential that the second engagement means be of circular cross-section although this is preferred. This has the advantage that fewer of the expensive head components are required to achieve this range of variables. Naturally the head will have to be provided in a number of incrementally varying sizes to fit the needs of each individual patient's scapula or glenoid prosthesis.

The portion of the engagement means forming part of the intermediate connecting member can both be male or alternatively one can be male and the other female.

It is further desired that the engagement means will each be of a substantially cylindrical shape, whether male or female, and therefore allow the intermediate connecting member to be rotatable relative to the stem and the head rotatable relative to the intermediate connecting member before securement. To fix one part relative to the other the cylinders of the male and female portions are preferably of the Morse taper type. This fixing may be supplemented by a screw fixing.

In order to satisfy the criterion for strength, it is desirable that the intermediate connecting member be formed in one piece. It is, however, within the scope of this invention that the intermediate connecting member be formed from a plurality of pieces.

BRIEF DESCRIPTION OF THE DRAWING

Embodiments of the invention will now be described by way of example and with reference to the accompanying schematic drawings, in which.

DETAILED DESCRIPTION OF PREFERRED EMBODIMENTS

Figures 1, 2:
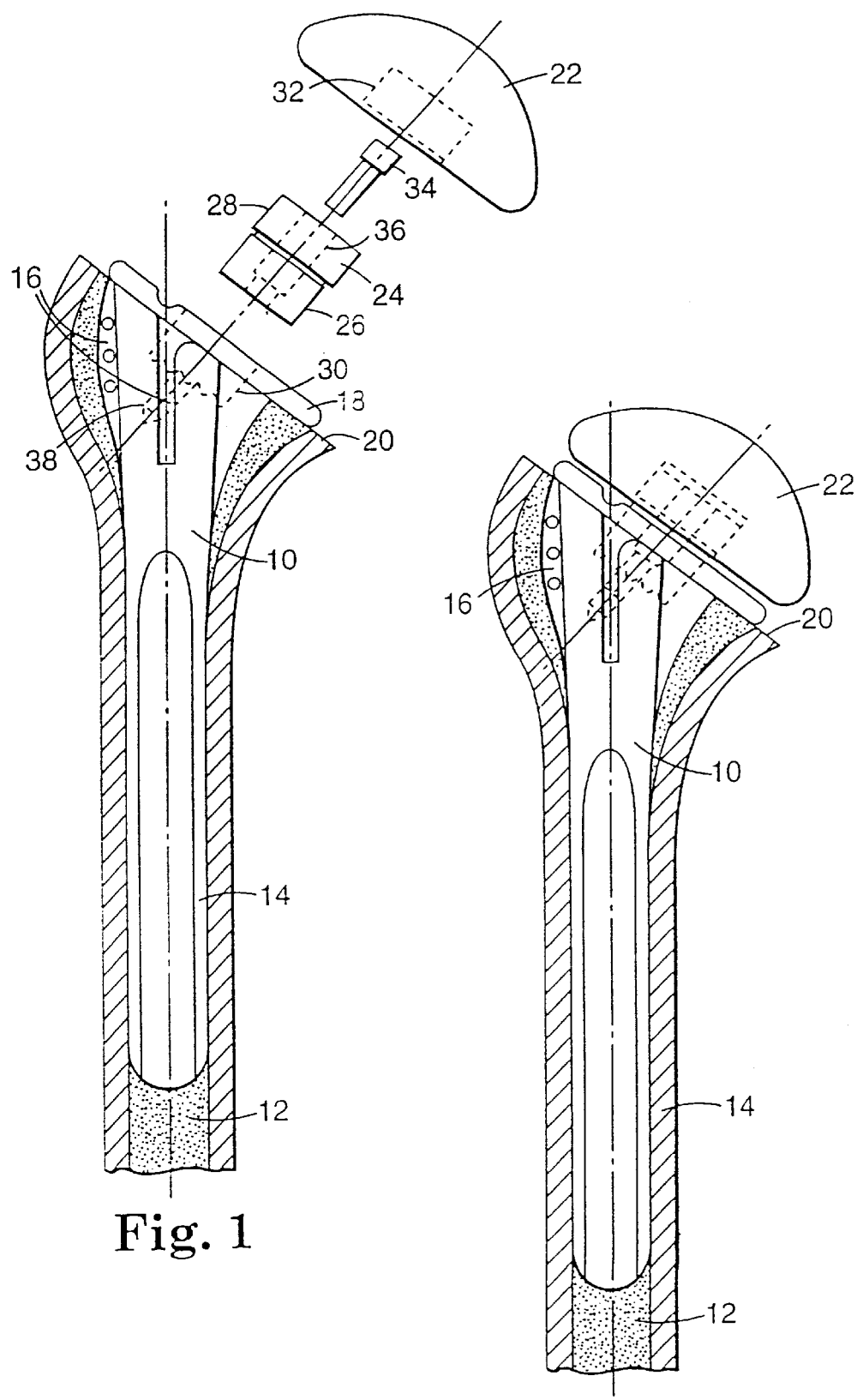
FIG. 1 is an exploded side elevation of a modular humeral prosthesis according to the invention.
FIG. 2 is the assembled prosthesis of FIG. 1.

The stem 10 shown in FIG. 1 is available in a number of different sizes to match the size to which the medullary canal 12 has been reamed or broached. The shaft of the stem 14 is designed to contact the previously reamed or broached medullary canal 12 and extend into the remaining humerus to prevent any movement of the stem 10.

The stem 10 is prevented from rotating by the use of fins 16 located at the neck of the stem 10. These fins 16 are wedged into the proximal position of the humerus to prevent any movement of the stem 10 and offer some additional support to the face 18 of the stem 10. The face 18 of the stem 10 fits onto the previously prepared face of the humerus 20, and is designed so that the angle of the face 18 is roughly equal to that of the anatomic neck of the humerus. Coassigned U.S. patent application Ser. No. 08/946,758, filed Oct. 8, 1997, and PCT International patent application No. US97/18207, filed Oct. 8, 1997, both by Michel Mansat et al., disclose a shoulder prosthesis with fins, and are incorporated herein by reference.

The humeral head 22 is designed to articulate with the scapula or glenoid prosthesis (not shown). The head 22 replaces the articulating surface of the humerus and is largely hemispherical in shape. A variety of sizes of head 22 are provided to complement the patient's scapula on glenoid prosthesis. The articulating surface of the head 22 is highly polished to reduce friction, hence wear on the scapula or glenoid prosthesis.

An intermediate connecting member 24 has first and second male tapers 26 and 28 of the "Morse taper" type. A "Morse taper" is taper that forms an angle providing a self-locking function. Once pushed together two Morse taper parts tend to stay together. The first taper 26 is designed to connect with the stem 10 and the second taper 28 with the head 22. The tapers 26 and 28 are aligned in generally opposite directions for mating with a female taper 30 of the stem 10 and a female taper 32 of the head 22.

The first male taper 26 may also be held onto the female taper 30 of the stem 10 by means of a locking screw 34, which fits into a counter-bored hole 36 in the intermediate connecting member 24. The axis of this counter-bored hole 36 is aligned along the central axis of the taper 26 and the screw fits into this counter-bored hole 36 and locates into a threaded hole 38 in the stem 10.

The male tapers 26, 28 of the intermediate connecting member 24 are securely connected with the respective female tapers 30, 32 of the stem 10 and head 22, which are also of the Morse taper type and match the tapers of the intermediate connecting member 24 by applying an external force, to form an interference fit between the mating tapers 24 and 30, and 26 and 32, as shown in FIG. 2.

It will be understood that the first and second male tapers 26 and 28 constitute one embodiment of the first and second engagement means of the intermediate connecting member 24. Alternatives include other connecting or mating parts that define the relative orientation and position of the head 22 and the intermediate connecting member 24 or the stem 10 and the intermediate connecting member 24. For example, the first and second male tapers 26 and 28 could be replaced by female tapers (not shown) and the female tapers 30 and 32 of the stem 10 and head 22 replaced by male tapers (not shown).

There can be a large variety in the shape, size and orientation of human humeral bones and therefore it is desirable to tailor the humeral prosthesis to suit each individual case. The various designs of intermediate connecting members of the present invention provide a massive range of different head positions and orientations relative to the humeral stem that can be selected and connected interoperatively.

The position of the head 22 can be varied by using different intermediate connecting members 24 as are appropriate in each individual case. Various designs of intermediate connecting members 24a–e are illustrated in FIGS. 3 to 7.

In each of these cases the intermediate connecting member 24a–e has the same elements and is joined to the stem 10 and head 22 as described above.

Figure 3:
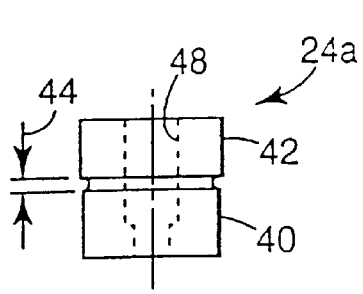
FIGS. 3 to 7 are various intermediate connecting members according to the first embodiment of the invention.

One configuration of an intermediate connecting member 24a is illustrated in FIG. 3. In this configuration, the first male taper 40 and the second male taper 42 are axially aligned with minimum separation or "neck length" 44 between them. The design of this intermediate connecting member 24a matches the anatomical design of some patients' original humerus.

Figure 4:
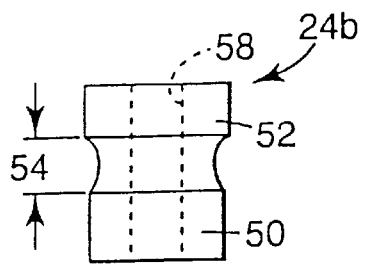

For other patients, a larger separation between the head 22 of the humeral prosthesis and a fixed point on the stem 10 is more appropriate. To meet this requirement, the intermediate connecting member 24b of FIG. 4 is used. In this design, a portion of the intermediate connecting member 24b between the two tapers 50 and 52 is available in a number of incrementally different sizes to allow the surgeon to select the appropriate separation or "neck length" 54 between the tapers 50 and 52, and hence the separation between the head 22 and stem 10 of the prosthesis.

Figure 5:
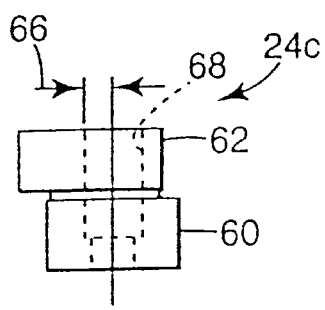

The anterior or posterior offset can be simulated using the design of intermediate connecting member 24c as shown in FIG. 5 to mimic offsets 66 that can naturally occur in the humerus. In this design, the central axii of the first and second male tapers 60 and 62 are parallel and offset from one another as illustrated at 66. The second male taper 62 is counter-bored at an off-center position (e.g., compare bore 68 or FIG. 5 with bores 48 and 58 of FIGS. 3 and 4). This allows the head 22 to be attached on a parallel but not coincident axis to the first male taper 60, and thus to the female taper 30 of the stem 10. Again, this design is available in a number of incrementally different offsets 66 so the surgeon can select the most appropriate intermediate connecting member 24c for each individual patient interoperatively.

Figure 6:
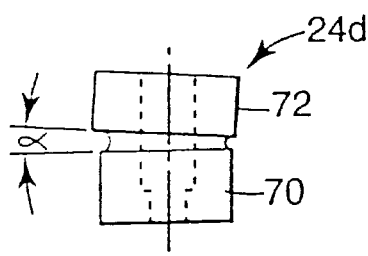

The angle of inclination α of the humeral head relative to the axis of the humeral stem can vary from patient to patient. The intermediate connecting member 24d can simulate this orientation. The design shown in FIG. 6 comprises a portion of the intermediate connecting member 24d that has a generally wedge-shaped design. The surgeon will be able to select the wedge-shaped intermediate connecting member 24d from a range of intermediate connecting members 24d having incremental difference in the inclination angle α as shown in FIG. 6, to best fit each individual patient. Due to the wedge-shape, the central axii of the first and second male tapers 70 and 72 of this design are offset from parallel by an angle equal to the inclination angle α.

Any of the features of intermediate connecting members 24a–d illustrated in FIGS. 3 to 6 can be combined to provide the desired variation in neck length 44, 54, 84 anterior or posterior offset 66, 86 or angular inclination a to best suit each individual patient's anatomy.

Figure 7:
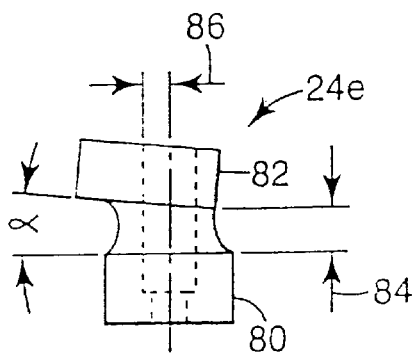

FIG. 7 shows an intermediate connecting member 24e that includes a combination of the angular inclination a as described in FIG. 6, the anterior/posterior offset 86 as depicted in FIG. 5, and the taper separation 84 as illustrated in FIG. 4.

Figure 8:
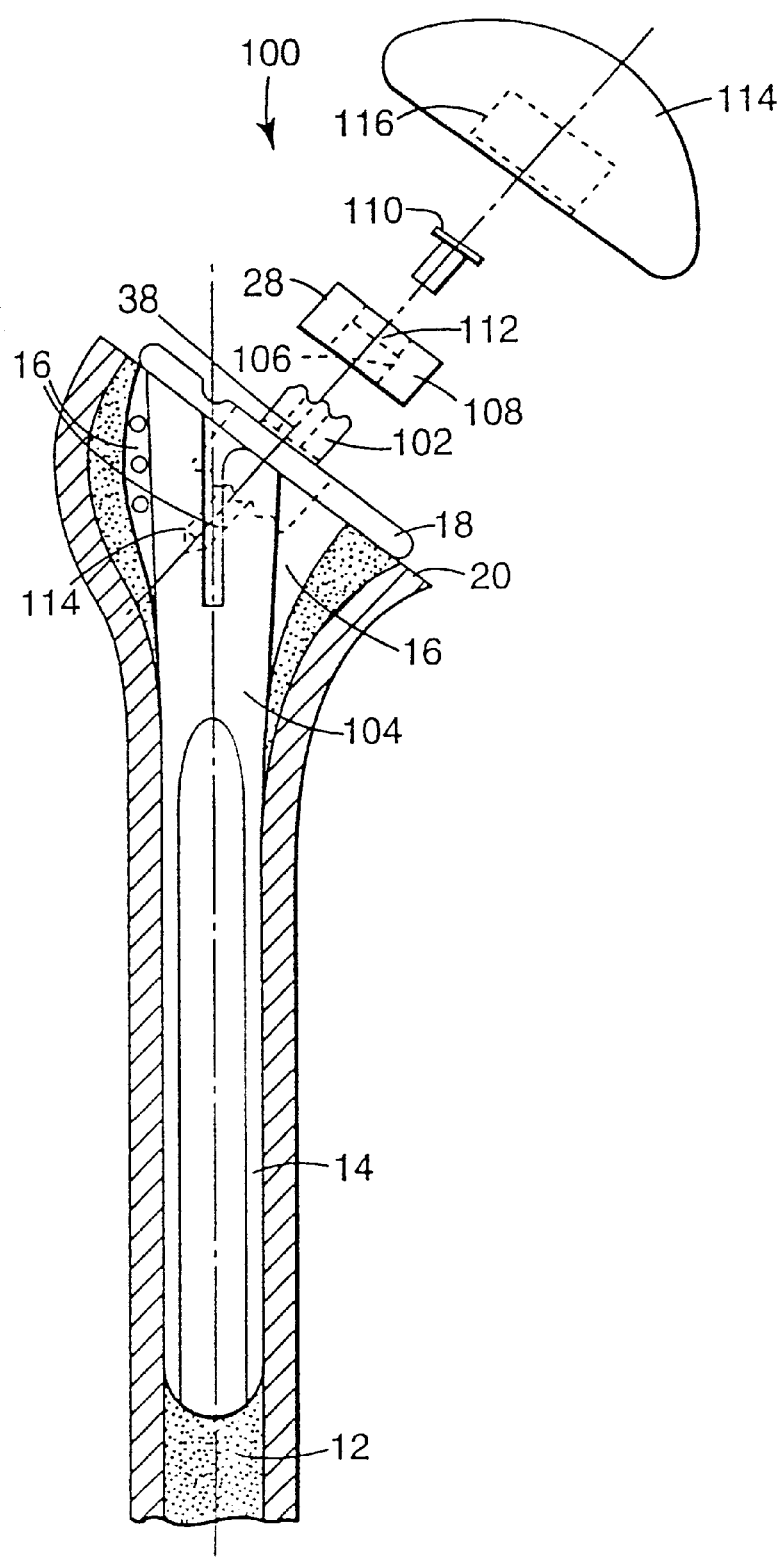
FIG. 8 is an exploded side elevation of a second embodiment of the modular humeral prosthesis according to the invention.

In the above embodiments, the male members of the two engagement means are provided by the intermediate connecting member 24a–e. In an alternative embodiment one or both of the two engagement means provided by the intermediate connecting member may comprise female portions. For example, FIG. 8 illustrates a second embodiment of the modular humeral prosthesis 100 of the invention similar in many respects to the first embodiment shown in FIGS. 1–7. Differences include the provision of a male tapered connecting portion 102 on the stem 104, and a female tapered connecting portion 106 on the intermediate connecting member 108.

Male connecting portion 102 and female connecting portion 106 are designed for substantially self-locking mating, and preferably have a circular cross section The self-locking function may be accomplished by providing a "Morse taper" on the male and female connecting portions 102 and 106. The female connecting portion 106 constitutes a second embodiment of the first engagement means of the intermediate connecting member 108.

A fastener 110 preferably is inserted through a bore 112 through the intermediate connecting member 108 and into engagement with a bore 114 in the stem 104 to further secure the female connecting portion 106 of the intermediate connecting member 108 on the stem 104. Most preferably, the fastener 110 and the bore 114 are provided with interlocking threads. As an alternative embodiment, the male and female connecting portion 102 and 106 could be provided with a non-self-locking configuration; in which case the fastener 110 or another locking mechanism would take on yet greater importance.

As is the case with the first embodiment, the head 114 of the second embodiment is provided with a female connecting portion 116, and the second engagement means of the intermediate connecting member 108 comprises a male connecting portion 118. The female and male connecting portions 116 and 118 are also preferably provided with a self-locking tapered configuration, i.e., a Morse taper.

Figure 9:
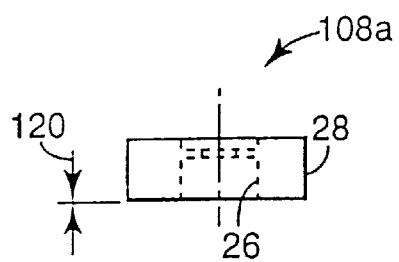
FIGS. 9–13 are various intermediate connecting members according to the second embodiment of the invention.
Figure 10:
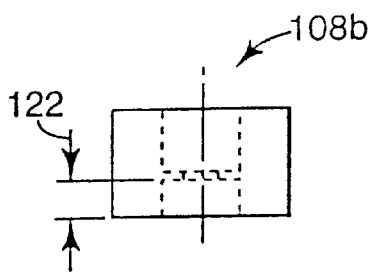

FIGS. 9–13 illustrate various intermediate connecting members 108a–e for use in the prosthesis 100. FIGS. 9 and 10 illustrate two intermediate connecting members 108a and 108b providing two different separations 120 and 122. In this respect, intermediate connecting member 108a is similar to intermediate connecting member 24a of the first embodiment (FIG. 3) due to the minimal separation 120 or 44, and intermediate connecting member 108b is similar to intermediate connecting member 24b of the first embodiment (FIG. 4) due to the greater separation 122 or 54. Both intermediate connecting member 108a and 108b show a zero inclination angle and a zero offset.

Figure 11:
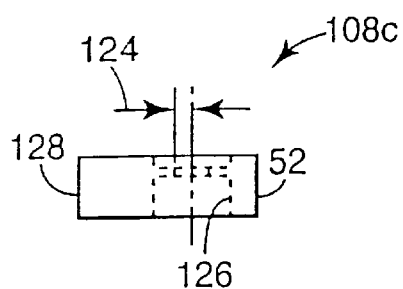

FIG. 11 illustrates another intermediate connecting member 108c having, like member 108a, minimal separation. Intermediate connecting member 108c, however, has a non-zero offset 124. This non-zero offset 124 is accomplished by displacing or offsetting the central axis or axis of rotation of the female locking portion 126 relative to the central axis of axis of rotation of the male locking portion 128 by the offset 124. In this respect, the intermediate connecting member 108c is similar to the intermediate connecting member 24c of the first embodiment (FIG. 5).

Figure 12:
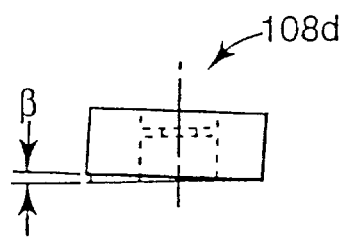

FIG. 12 illustrates yet another intermediate connecting member 108d having, like member 108a, minimal separation and zero offset. Intermediate connecting member 108d, however, has a non-zero inclination angle β. Inclination angle β is similar in function and preferred magnitude to the inclination angle α discussed with respect to the first embodiment (e.g., FIG. 6).

Figure 13:
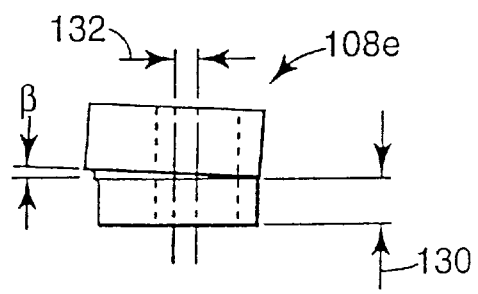
Figure 14:
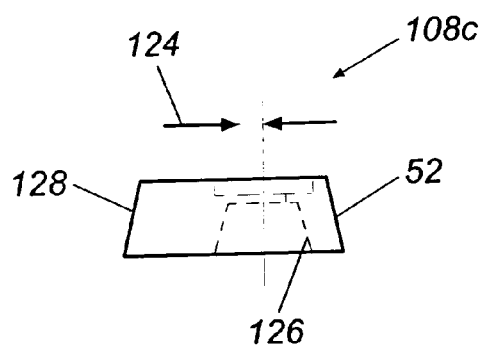
FIGS. 14–16 are various intermediate connecting members according to an embodiment of the invention having tapered locking mechanisms.
Figure 15:
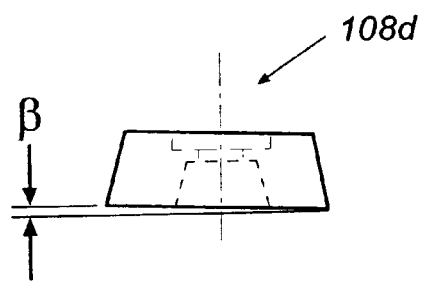
Figure 16:
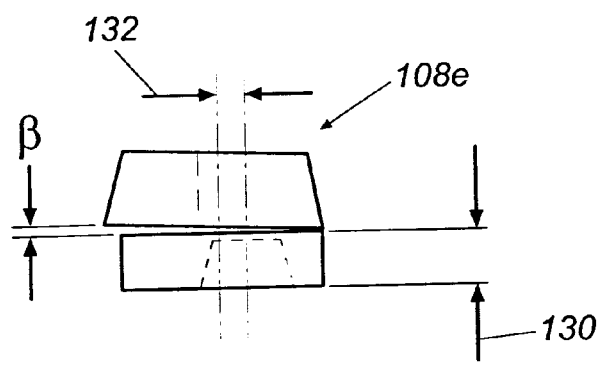

FIG. 13 illustrates an intermediate connecting member 108e having a non-zero separation 130, a non-zero offset 132 and a non-zero inclination angle β. In this respect, intermediate connecting member 108e is similar to intermediate connecting member 24e of the first embodiment (FIG. 7).

One consequence of the design of the second embodiment of the prosthesis is that the male connecting portion 102 may have a length extending into the intermediate connecting member, e.g., 108a, a distance sufficient that it is received both in the intermediate connecting member 108a and the void defined by the female connecting portion 116 of the head 114. This is accomplished, of course, without any direct engagement between the male connecting portion 102 of the stem 104 and the female connecting portion 116 of the head 114.

Other embodiments, which are not illustrated in the drawing, include (1) the first engagement means comprising a male connecting portion and the second engagement means to comprising a female connecting portion, and (2) both the first and second engagement means comprising female portions.

As various changes could be made in the above constructions and methods without departing from the scope of the invention as defined in the claims, it is intended that all matter contained in the above description or shown in the accompanying drawings be interpreted as illustrative and not in a limiting sense.

What is claimed is:

1. A modular humeral prosthesis for replacement of the humeral head of a humerus, comprising:
   (a) a stem adapted to be fitted to a resected humerus;
   (b) a head adapted to approximate the size and shape of a humeral head;
   (c) an intermediate connecting member for connecting the stem to the head, the intermediate connecting member including:
      a first connector that is formed as a surface of rotation and adapted to cooperate with the stem in order to mount the intermediate connecting member to the stem, the first connector comprising an opening adapted to receive a fastener;
      a second connector that is formed as a surface of rotation and adapted to cooperate with the head in order to mount the head to the intermediate connecting member, the second connector comprising an opening adapted to receive a fastener; and
      a fastener adapted to be inserted through the openings in the first and second connectors and to fasten the intermediate connecting member to the stem.

2. A prosthesis according to claim 1 in which the second connector includes a self-locking tapered surface.

3. A prosthesis according to claim 2 in which the first connector is adapted to be at least partially received in a cavity of the stem and features a self-locking tapered surface.

4. A prosthesis according to claim 2 in which the first connector is a cavity formed in the second connector and adapted at least partially to receive a projection that projects from the stem.

5. A prosthesis according to claim 1 in which the second connector is a cavity formed in the first connector and adapted at least partially to receive a projection that projects from the head.

6. A prosthesis according to claim 1 in which the intermediate connecting member is adapted to rotate 360 degrees relative to each of the stem and the head.

7. A prosthesis according to claim 1 in which the stem features a face and the fastener is adapted to be inserted into the stem in a direction that is substantially perpendicular to the face.

8. A prosthesis according to claim 1 in which the second connector is inclined at an angle relative to the first connector.

9. A prosthesis according to claim 1 in which each of the first connector and second connector have an axis, and in which said axes are offset from each other in order to cause the first connector to be offset from the second connector.

10. A modular humeral prosthesis for replacement of the humeral head of a humerus, comprising:
    (a) a stem adapted to be fitted to a resected humerus, the stem featuring a face;
    (b) a head adapted to approximate the size and shape of a humeral head;
    (c) an intermediate connecting member for connecting the stem to the head, the intermediate connecting member including:
       a first connector adapted to cooperate with stem structure to mount the stem to the intermediate connecting member, the first connector generally circular in cross section and including a self locking taper, the first connector comprising an opening adapted to receive a fastener;
       a second connector adapted to cooperate with head structure to mount the head to the intermediate connecting member, the second connector generally circular in cross section and including a self locking taper that is adapted to mount the intermediate connecting member to the head, the second connector comprising an opening adapted to receive a fastener; and
       a fastener adapted to be inserted through the opening in the connectors and into the stem in a direction substantially perpendicular to the face and thereby to fasten the intermediate connecting member to the stem.

11. A prosthesis according to claim 10 in which the first connector is a male structure adapted to be received at least partially in a cavity in the stem.

12. A prosthesis according to claim 10 in which the second connector is a male structure adapted to be received at least partially in a cavity in the head.

13. A modular humeral prosthesis kit for replacement of the humeral head of a humerus, comprising:
    (a) a stem to be fitted to a resected humerus;
    (b) a head sized and configured to approximate the humeral head;
    (c) a plurality of intermediate connecting members of which one may be selected to connect the stem to the head, each intermediate connecting member comprising:
       a first connector formed as a surface of rotation and adapted to cooperate with the stem in order to mount the intermediate connecting member to the stem, the first connector comprising an opening adapted to receive a fastener;
       a second connector formed as a surface of rotation and adapted to cooperate with the head in order to mount the head to the intermediate connecting member, the second connector comprising an opening adapted to receive a fastener; and a fastener adapted to be inserted through the openings in the first and second connectors and to fasten the intermediate connecting member to the stem;

(d) the intermediate connecting members of the kit comprising:

at least one intermediate connecting member in which the surfaces of rotation of each of the first and second connectors share the same axis of rotation;

at least one intermediate connecting member in which the surfaces of rotation of each of the first and second connectors are generally parallel to each other but offset; and at least one intermediate connecting member in which the surfaces of rotation of each of the first and second connectors are inclined at an angle relative to each other, causing the first and second connectors to be inclined at an angle relative to each other.

14. A kit according to claim 13 in which the second connector of each intermediate connecting member includes a self-locking tapered surface.

15. A kit according to claim 14 in which the first connector of each intermediate connecting member is adapted to be at least partially received in a cavity of the stem and features a self-locking tapered surface.

16. A kit according to claim 14 in which the first connector of each intermediate connecting member is a cavity formed in the second connector and adapted at least partially to receive a projection that projects from the stem.

17. A kit according to claim 13 in which the second connector of each intermediate connecting member is a cavity formed in the first connector and adapted at least partially to receive a projection that projects from the head.

18. A kit according to claim 13 in which each intermediate connecting member is adapted to rotate 360 degrees relative to each of the stem and the head.

19. A kit according to claim 13 in which the stem features a face and the fastener is adapted to be inserted into the stem in a direction that is substantially perpendicular to the face.

20. A method of replacing a humeral head in a patient, comprising:

(a) resecting the proximal end of the humerus to remove the head and expose the medullary canal of the humerus;

(b) inserting a stem of a prosthesis into the medullary canal of the resected humerus, the prosthesis comprising:

(i) the stem;

(ii) a head adapted to approximate the size and shape of a humeral head;

(iii) one of a plurality of intermediate connecting members for connecting the stem to the head, each intermediate connecting member including:

a first connector formed as a surface of rotation and adapted to cooperate with the stem in order to mount the intermediate connecting member to the stem, the first connector comprising an opening adapted to receive a fastener;

a second connector formed as a surface of rotation and adapted to cooperate with the head in order to mount the head to the intermediate connecting member, the second connector comprising an opening adapted to receive a fastener; and a fastener adapted to be inserted through the openings in the first and second connectors and to fasten the intermediate connecting member to the stem;

the plurality of intermediate connecting members including at least some members having different angles of inclination between their first and second connectors;

(c) selecting a particular intermediate connecting member to provide a desired angle of inclination of the head relative to the humerus; and (d) inserting the fastener through the first and second connectors and into the stem to mount the intermediate connecting member to the stem, and mounting the intermediate connecting member to the head, the mounting of the intermediate connecting member to the stem and head imparting the desired angle of inclination of the head relative to the humerus.

21. A modular humeral prosthesis for replacement of the humeral head of a humerus, comprising:

(a) a stem adapted to be fitted to a resected humerus;

(b) a head adapted to approximate the size and shape of a humeral head;

(c) an intermediate connecting member for connecting the stem to the head, the intermediate connecting member including:

a first connecting surface that is adapted to cooperate with structure forming part of the stem in order to mount the intermediate connecting member to the stem; and a second connecting surface adapted to cooperate with structure forming part of the head in order to mount the head to the intermediate connecting member, the second connecting surface at least partially nested with the first connecting surface and the first and second surfaces being surfaces of rotation having axes of rotation, the axis of rotation of the first surface non-collinear with the axis of rotation of the second surface.

22. A prosthesis according to claim 21 in which both connecting surfaces are adapted to lock to corresponding structure using a tapered locking mechanism.

23. A prosthesis according to claim 21 in which the second connecting surface is inclined at an angle relative to the first connecting surface.

24. A prosthesis according to claim 21 in which each of the first connecting surface and the second connecting surface has an axis, and in which said axes are offset from each other in order to cause the first connecting surface to be offset from the second connecting surface.

25. A prosthesis according to claim 21 in which each of the first connecting surface and the second connecting surface has an axis, and in which said axes do not coincide with each other in order to cause the first connecting surface to be non-coaxial with the second connecting surface.

26. A modular humeral prosthesis according to claim 21 in which the first connecting surface is a female connecting surface and the second connecting surface is a male connecting surface.

27. A modular humeral prosthesis for replacement of the humeral head of a humerus, comprising:

(a) a stem adapted to be fitted to a resected humerus;

(b) a head adapted to approximate the size and shape of a humeral head;

(c) an intermediate connecting member for connecting the stem to the head, the intermediate connecting member including:

a first connecting surface forming a tapered, generally frustoconically shaped, cavity that is adapted to cooperate with a structure forming part of the stem in order to mount and lock the intermediate connecting member to the stem; and a second connecting surface that is generally frustoconically shaped, tapered, and adapted to cooperate with structure forming part of the head in order to mount and lock the head to the intermediate connecting member, the second connecting surface at least partially nested with the first connecting surface and the first and second surfaces being surfaces of rotation having axes of rotation, the axis of rotation of the first surface non-collinear with the axis of rotation of the second surface.

28. A prosthesis according to claim 27 in which the second connecting surface is inclined at an angle relative to the first connecting surface.

29. A prosthesis according to claim 27 in which each of the first connecting surface and the second connecting surface has an axis, and in which said axes are offset from each other in order to cause the first connecting surface to be offset from the second connecting surface.

30. A prosthesis according to claim 27 in which each of the first connecting surface and the second connecting surface has an axis, and in which said axes do not coincide with each other in order to cause the first connecting surface to be non-coaxial with the second connecting surface.

31. A modular humeral prosthesis according to claim 27 the first connecting surface is a female connecting surface and the second connecting surface is a male connecting surface.

32. A modular humeral prosthesis kit for replacement of the humeral head of a humerus, comprising:

(a) a stem to be fitted to a resected humerus;

(b) a head sized and configured to approximate the humeral head;

(c) a plurality of intermediate connecting members of which one may be selected to connect the stem to the head, each intermediate connecting member comprising:

a first, female, connecting surface forming a cavity that is adapted to receive a structure that protrudes from the stem in order to mount the intermediate connecting member to the stem; and a second, male, connecting surface adapted to be received in a cavity in the head in order to mount the head to the intermediate connecting member, the second connecting surface at least partially nested with the first connecting surface;

(d) the intermediate connecting members of the kit comprising:

at least one intermediate connecting member in which the first and second connecting surfaces share an axis of rotation;

at least one intermediate connecting member in which the first and second connecting surfaces are offset from each other; and at least one intermediate connecting member in which the first and second connecting surfaces are inclined at an angle relative to each other.

33. A prosthesis kit according to claim 32 in which both connecting surfaces are adapted to lock to corresponding structure using a tapered locking mechanism.

34. A method of replacing a humeral head in a patient, comprising:

(a) resecting the proximal end of the humerus to remove the head and expose the medullary canal of the humerus;

(b) inserting a stem of a prosthesis into the medullary canal of the resected humerus, the prosthesis comprising:

(i) the stem;

(ii) a head adapted to approximate the size and shape of a humeral head;

(iii) one of a plurality of intermediate connecting members for connecting the stem to the head, each intermediate connecting member including:

a first, female, connecting surface forming a cavity that is adapted to receive structure that protrudes from the stem in order to mount the intermediate connecting member to the stem; and a second, male, connecting surface adapted to be received in a cavity in the head in order to mount the head to the intermediate connecting member, the second connecting surface at least partially nested with the first connecting surface;

the plurality of intermediate connecting members including at least some members having different angles of inclination between their first and second connectors;

(c) selecting a particular intermediate connecting member to provide a desired angle of inclination of the head relative to the humerus; and (d) mounting and locking the intermediate connecting member to the stem, and mounting and locking the intermediate connecting member to the head, the mounting and locking of the intermediate connecting member to the stem and head imparting any desired angle of inclination of the head relative to the humerus.

35. A modular humeral prosthesis for replacement of the humeral head of a humerus, comprising:

(a) a stem adapted to be fitted to a resected humerus;

(b) a head adapted to approximate the size and shape of a humeral head;

(c) an intermediate connecting member for connecting the stem to the head, the intermediate connecting member including:

a first, female, connecting surface forming a cavity that is adapted to receive structure that protrudes from the stem in order to mount the intermediate connecting member to the stem; and a second, male, connecting surface adapted to be received in a cavity in the head in order to mount the head to the intermediate connecting member, the second connecting surface at least partially nested with the first connecting surface and the first and second surfaces being non-coaxial.

36. A modular humeral prosthesis for replacement of the humeral head of a humerus, comprising:

(a) a stem adapted to be fitted to a resected humerus;

(b) a head adapted to approximate the size and shape of a humeral head;

(c) an intermediate connecting member for connecting the stem to the head, the intermediate connecting member including:

a first, female, connecting surface forming a tapered, generally frustoconically shaped, cavity that is adapted to receive a structure that protrudes from the stem in order to mount and lock the intermediate connecting member to the stem; and a second, male, connecting surface that is generally frustoconically shaped, tapered, and adapted to be received in a cavity in the head in order to mount and lock the head to the intermediate connecting member, the second connecting surface at least partially nested with the first connecting surface and the first and second surfaces being non-coaxial.

37. A method of replacing a humeral head in a patient, comprising:
- (a) resecting the proximal end of the humerus to remove the head and expose the medullary canal of the humerus;
- (b) inserting a stem of a prosthesis into the medullary canal of the resected humerus, the prosthesis comprising:
  - (i) the stem;
  - (ii) a head adapted to approximate the size and shape of a humeral head;
  - (iii) one of a plurality of intermediate connecting members for connecting the stem to the head, each intermediate connecting member including:
    - a first connector formed as a surface of rotation and adapted to cooperate with the stem in order to mount the intermediate connecting member to the stem,
    - a second connector formed as a surface of rotation and adapted to cooperate with the head in order to mount the head to the intermediate connecting member the second connector surface at least partially nested with the first connector surface,
    - the plurality of intermediate connecting members including at least some members having different angles of inclination between their first and second connectors;
- (c) selecting a particular intermediate connecting member to provide a desired angle of inclination of the head relative to the humerus; and
- (d) mounting the intermediate connecting member to the stem, mounting the intermediate connecting member to the head, the mounting of the intermediate connecting member to the stem and head imparting the desired angle of inclination of the head relative to the humerus.

38. A method of replacing a humeral head in a patient, comprising:
- (a) resecting the proximal end of the humerus to remove the head and expose the medullary canal of the humerus;
- (b) inserting a stem of a prosthesis into the medullary canal of the resected humerus, the prosthesis comprising:
  - (i) the stem;
  - (ii) a head adapted to approximate the size and shape of a humeral head;
  - (iii) one of a plurality of intermediate connecting members for connecting the stem to the head, each intermediate connecting member including:
    - a first connector formed as a surface of rotation and adapted to cooperate with the stem in order to mount the intermediate connecting member to the stem,
    - a second connector formed as a surface of rotation and adapted to cooperate with the head in order to mount the head to the intermediate connecting member the second connector surface at least partially nested with the first connector surface,
    - the plurality of intermediate connecting members including at least some members with each of the first connector and second connector having an axis, and in which said axes are offset from each other in order to cause the first connector to be offset from the second connector,
- (c) selecting a particular intermediate connecting member to provide a desired offset of the head relative to the stem; and
- (d) mounting the intermediate connecting member to the stem, mounting the intermediate connecting member to the head, the mounting of the intermediate connecting member to the stem and head imparting the desired offset of the head relative to the humerus.

* * * * *